(12) United States Patent
Winstanley et al.

(10) Patent No.: US 11,033,288 B2
(45) Date of Patent: Jun. 15, 2021

(54) END EFFECTORS ACTUATION PLATFORM

(71) Applicant: UNITED STATES ENDOSCOPY GROUP, INC., Mentor, OH (US)

(72) Inventors: John P. Winstanley, Madison, OH (US); Keith R. John, Chardon, OH (US); Paul Martino, Solon, OH (US); Joseph Michelini, Spring Lake, MI (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 125 days.

(21) Appl. No.: 16/192,757

(22) Filed: Nov. 15, 2018

(65) Prior Publication Data

US 2019/0150968 A1 May 23, 2019

Related U.S. Application Data

(60) Provisional application No. 62/586,515, filed on Nov. 15, 2017, provisional application No. 62/586,573, filed on Nov. 15, 2017.

(51) Int. Cl.
*A61B 17/29* (2006.01)
*A61B 10/06* (2006.01)
(Continued)

(52) U.S. Cl.
CPC .......... *A61B 17/29* (2013.01); *A61B 1/00087* (2013.01); *A61B 10/06* (2013.01);
(Continued)

(58) Field of Classification Search
CPC ............ A61B 10/06; A61B 2017/2902; A61B 2017/2939; A61B 2017/2912; A61B 17/29
See application file for complete search history.

(56) References Cited

U.S. PATENT DOCUMENTS 3,895,636 A   7/1975 Schmidt
5,172,700 A   12/1992 Bencini et al.
(Continued)

FOREIGN PATENT DOCUMENTS

EP   0945105 A1   9/1999
JP   3708552 B2   10/2005

OTHER PUBLICATIONS

Invitation to Pay Additional Fees from PCT/US2018/061392 dated Feb. 8, 2019 (15 pages).
(Continued)

*Primary Examiner* — Alexander J Orkin
(74) *Attorney, Agent, or Firm* — Calfee Halter & Griswold LLP

(57) ABSTRACT

An endoscopic device includes a base, one or more end effectors, and an actuating assembly. The base includes a cylindrical shaft will a hollow interior. The end effectors are connected to the distal portion of the base such that the end effectors are movable between open and closed positions. The actuating assembly moves the end effectors between the open and closed position. The actuating assembly includes a driver that has at least one stopper feature extending radially from the driver shaft. The driver of the actuating assembly is at least partially disposed within the hollow interior of the base such that the stopper feature is movable in an opening of the base. The stopper feature engages a distal edge of the opening to prevent movement of the driver in a distal direction relative to the base and engages a proximal edge of the opening to prevent movement of the driver in a proximal direction relative to the base. Movement of the driver in the distal direction causes the end effectors to move to the open position, and movement of the driver in the proximal direction causes the end effectors to move to the closed position.

3 Claims, 21 Drawing Sheets

(51) Int. Cl.
*A61B 1/00* (2006.01)
*A61B 17/00* (2006.01)

(52) U.S. Cl.
CPC .............. *A61B 17/00234* (2013.01); *A61B 2017/2902* (2013.01); *A61B 2017/2912* (2013.01); *A61B 2017/2939* (2013.01)

(56) References Cited

U.S. PATENT DOCUMENTS

| | | | | |
|---|---|---|---|---|
| 5,275,615 | A | * | 1/1994 | Rose ............... A61B 17/29 606/207 |
| 5,290,309 | A | | 3/1994 | Kothe |
| 5,471,992 | A | * | 12/1995 | Banik ............... A61B 10/0266 600/564 |
| 5,746,216 | A | | 5/1998 | Turturro et al. |
| 5,762,069 | A | * | 6/1998 | Kelleher ............... A61B 10/06 600/564 |
| 5,843,000 | A | * | 12/1998 | Nishioka ............... A61B 10/06 600/566 |
| 5,871,433 | A | * | 2/1999 | Lehmann ............... B65H 29/32 270/32 |
| 5,871,453 | A | | 2/1999 | Banik |
| 5,964,779 | A | | 10/1999 | Mayenberger |
| 6,086,606 | A | * | 7/2000 | Knodel ............... A61B 17/29 606/174 |
| 6,155,988 | A | * | 12/2000 | Peters ............... A61B 10/06 600/564 |
| 6,159,162 | A | | 12/2000 | Kostylev et al. |
| 2003/0018331 | A1 | | 1/2003 | Dycus et al. |
| 2005/0043758 | A1 | | 2/2005 | Golden et al. |
| 2012/0016391 | A1 | | 1/2012 | Aguirre |
| 2012/0109160 | A1 | * | 5/2012 | Martinez ............... A61B 17/10 606/142 |
| 2012/0165863 | A1 | * | 6/2012 | McLawhorn ......... A61B 17/29 606/207 |
| 2012/0197253 | A1 | | 8/2012 | Nishimura |
| 2015/0005813 | A1 | | 1/2015 | Maslanka |
| 2016/0100851 | A1 | | 4/2016 | Van Andel |

OTHER PUBLICATIONS

International Search Report and Written Opinion from PCT/US2018/061392 dated Apr. 9, 2019 (21 pages).
Invitation to Pay Additional Fees from PCT/US2018/061389 dated Feb. 12, 2019 (13 pages).
International Search Report and Written Opinion from PCT/US2018/061389 dated Apr. 9, 2019 (18 pages).
Office Action from U.S. Appl. No. 16/192,750 dated Jun. 8, 2020.

* cited by examiner

END EFFECTORS ACTUATION PLATFORM

CROSS-REFERENCE TO RELATED APPLICATIONS

The present application claims benefits and priority to U.S. Provisional Patent Application No. 62/586,573, filed on Nov. 15, 2017, and U.S. Provisional Patent Application No. 62/586,515, filed on Nov. 15, 2017, the entire disclosures of which are incorporated herein by reference.

FIELD OF THE INVENTION

The various embodiments relate to any end effectors at the distal portion of an endoscopic device like forceps for example, having a stopper feature on a drive arm to determine the maximum angle a pair of jaws can open when actuating the jaws. The actuation feature can be used to actuate jaws on endoscopic forceps but is not limited to such a use.

BACKGROUND INFORMATION

Conventional endoscopic devices, such as biopsy forceps, typically contain drive arms. Having at least two drive arms, the conventional endoscopic forceps extend outward from a longitudinal axis of the device when a conventional jaw assembly is opened and closed. The drive arms can limit a user's visibility when locating the tissue sample to take, and result in a longer rigid length which limits its ability to pass through an articulated scope. It can also cause tissue damage during electro-cauterization because the surrounding tissue is not easily insulated from the conductive drive wires. These and other problems exist with conventional endoscopic devices.

Improvements to forceps or other devices requiring end effectors can be made by improving the drive mechanism of the jaws such that the driver only extends in a longitudinal direction and not outward from the overall outer profile of the device.

SUMMARY OF THE INVENTION

An exemplary embodiment of an endoscopic device includes a base, one or more end effectors, and an actuating assembly. The base includes a cylindrical shaft will a hollow interior, in which the cylindrical shaft has a proximal portion and a distal portion, and in which the proximal portion has at least one opening. The end effectors are connected to the distal portion of the base such that the end effectors are movable between open and closed positions. The actuating assembly moves the end effectors between the open and closed position. The actuating assembly includes a driver that has a driver shaft, a proximal end, a distal end, and at least one stopper feature extending radially from the driver shaft. The driver of the actuating assembly is at least partially disposed within the hollow interior of the base such that the stopper feature is movable in the proximal opening of the base. The stopper feature engages a distal edge of the proximal opening to prevent movement of the driver in a distal direction relative to the base and engages a proximal edge of the proximal opening to prevent movement of the driver in a proximal direction relative to the base. Movement of the driver in the distal direction causes the end effectors to move to the open position, and movement of the driver in the proximal direction causes the end effectors to move to the closed position.

An exemplary embodiment of a method of using a driver of an actuator assembly to move at least one end effector that is connected to a base between an open position and a closed position includes pushing the river through at least a portion of a hollow interior of the base in a distal direction relative to the base until at least one stopper feature of the driver abuts a distal edge of an opening in the base. The end effector is in the open position when the stopper feature abuts the distal edge of the opening. The method also includes pulling the driver through at least a portion of the hollow interior of the base in a proximal direction until the stopper feature abuts a proximal edge of the opening in the base. The end effector is in a closed position when the stopper feature abuts the proximal edge of the opening.

Another exemplary embodiment of an endoscopic device includes a base, a driver, and a connector. The base has a first base component and a second base component, in which both the first base component and the second base component have a proximal portion and a distal portion. The proximal portion of both the first and second base components includes an opening. The first base component has one or more first base connectors, and the second base component has one or more second base connectors. The first base connectors are configured to connect to the second base connectors such that the first and second base components form a cylindrical shaft with a hollow interior. The driver has a driver shaft, a proximal end, a distal end, and at least one stopper feature extending radially from the driver shaft. The stopper feature is movable with at least one of the openings of the first and second base components when the first base connectors of the first base component are connected to the second base connectors of the second base component. The connector is configured to connect to the proximal end of both the first base component and the second base component to hold the first and second base components together when the first base connectors are not connected to the second base connectors.

These and aspects of the exemplary embodiments will become apparent from the following detailed description, taken in conjunction with the accompanying drawings, illustrating by way of example the principles of the various exemplary embodiments.

BRIEF DESCRIPTION OF THE DRAWINGS

In order to facilitate a fuller understanding of the exemplary embodiments, reference is now made to the appended drawings. These drawings should not be construed as limiting, but are intended to be exemplary only.

DETAILED DESCRIPTION OF EMBODIMENTS

Figure 1:
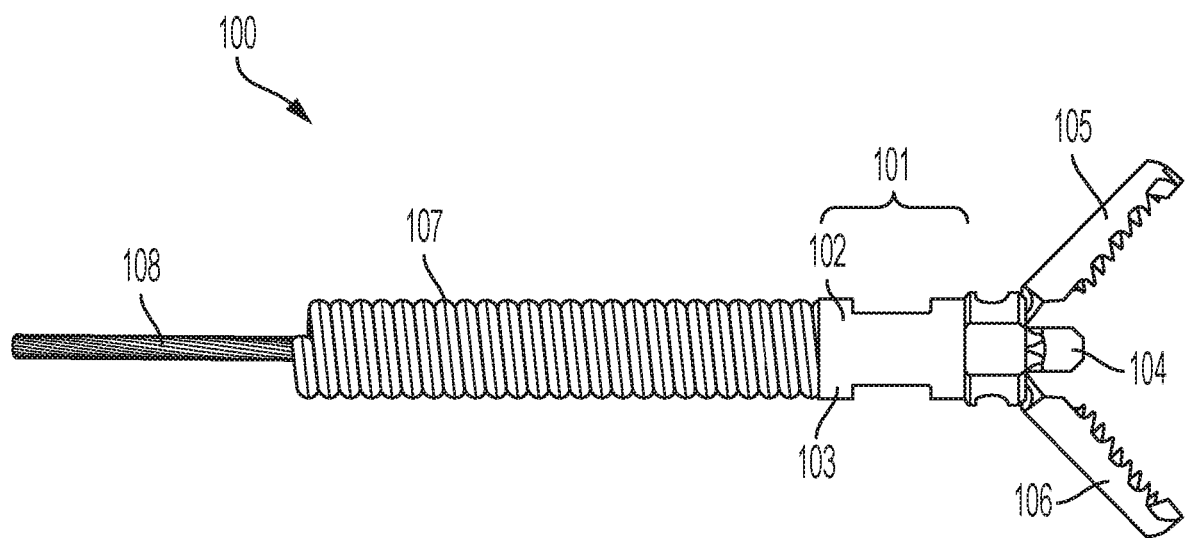
FIG. 1 depicts a side view of an exemplary embodiment of forceps.

The following description is intended to convey a thorough understanding of the embodiments by providing various embodiments and details involving a driver assembly for forceps. It is understood, however, that the invention is not limited to these specific embodiments and details, which are exemplary only. It is further understood that one possessing ordinary skill in the art, in light of known devices, systems and methods, would appreciate the use of the invention for its intended purposes and benefits in any number of alternative embodiments.

Generally speaking, the driver assembly for various end effectors could be utilized, but as an example, forceps were chosen. The forceps of the various exemplary embodiments described herein have at least one stopper on the driver that engages with the sidewalls of at least one opening in the base, such that when the stopper engages with the distal-most wall in the base opening, jaws or any other grasping tools attached to the distal end of the assembly are in a fully opened position. Similarly, when the at least one stopper on the driver is abutting the proximal-most wall in the base opening, jaws or any other grasping tools attached to the distal end of the assembly are in a fully closed position. Having a stopper that prevents a driver assembly from continuing movement (and thus providing a force to the jaws or other grasping tools) is advantageous because it prevents the jaws from disengaging with the base and/or drive assembly and prevents overtravel of the jaws to a more open position than desired.

In an exemplary embodiment, a device for obtaining a tissue sample has a base, where the base has a cylindrical shaft with a hollow interior, open distal end, and open proximal end, a first distal opening and a second distal opening along a distal portion of the shaft, and a first proximal opening and a second proximal opening along the shaft proximal of the first and second distal openings. The center of the shaft of the base defines a longitudinal axis. The device also has a driver with a shaft, a proximal end, a distal end, and at least one stopper feature extending radially from a shaft of the driver. The first and second proximal openings of the base having a distal edge and a proximal edge such that the at least one stopper feature abuts the distal edge of the proximal opening when the driver is moved distally in relation to the base, and the at least one stopper feature abuts the proximal edge of the proximal opening when the driver is moved proximally in relation to the base.

A method of using an exemplary embodiment of a device having a jaw assembly to obtain a tissue sample includes the step of opening a pair of jaws by pushing one or more drive wires in a distal direction to cause one of more drive member to move in a distal direction. The distal movement of the drive arm initiates opening of the distal ends of the jaw members apart from each other by pushing on an outer surface of each of at least two internal jaw arms, and the drive member also engages with the proximal ends of the internal jaw arms to push on the proximal of the internal jaw arms until the jaws are in a fully opened position. A method of using exemplary embodiment of the invention to obtain a tissue sample also includes closing the pair of jaws around a volume of tissue, This can include the steps of pulling a drive member or members in a proximal direction, to cause the distal surface of the internal jaw arms to pull the internal jaw arms in a proximal direction until the jaws are in a closed position and have grasped a tissue volume. The tissue can then be torn or removed from the body.

In certain embodiments, the method includes the steps of pushing a drive arm forward in a distal direction at least partially through a base until at least one stopper feature abuts a distal edge of an opening in the base, where a pair of jaws are opened; and pulling a drive arm backward in a proximal direction at least partially through a base until the at least one stopper feature abuts a proximal edge of the opening in the base, such that the jaws are closed.

The various exemplary embodiments generally describe devices that have a single drive arm that can be used to open and close a pair of jaws that tear or pull a volume of tissue away from a greater volume of tissue. However, the various embodiments are not so limited. For example, in various embodiments, various style jaws can be used on the device, and various extensions can exist on the distal end of the driver, such as to pierce or cauterize tissue.

Figure 2:
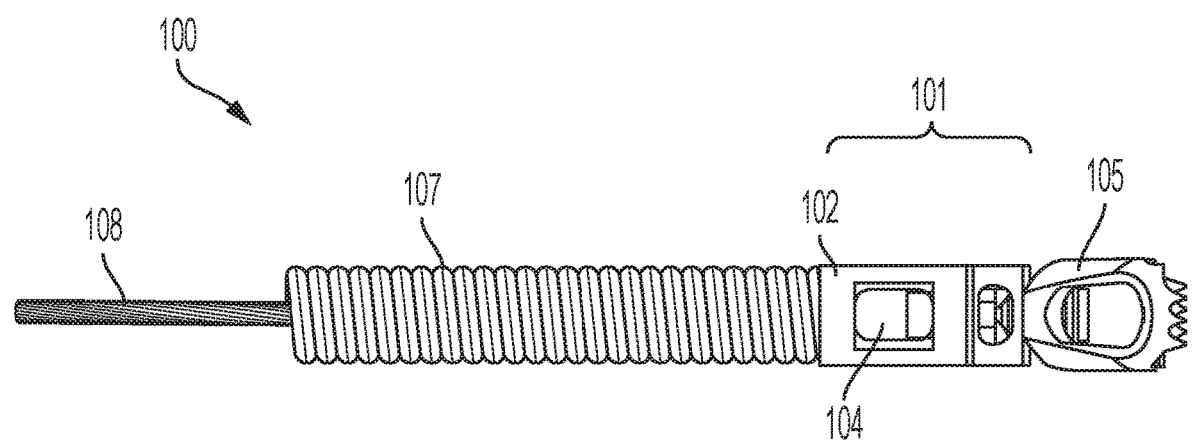
FIG. 2 depicts a top view of the forceps of FIG. 1.
Figure 3:
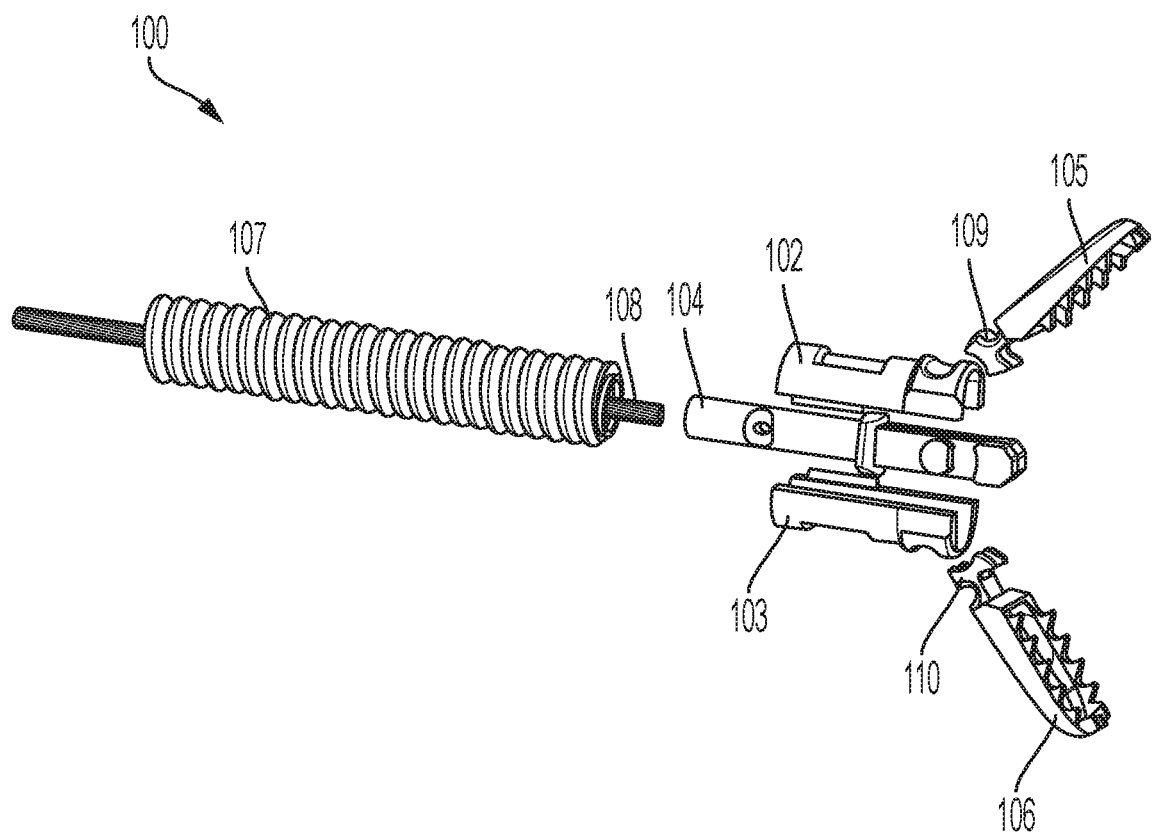
FIG. 3 depicts an exploded view of The forceps of FIG. 1.

FIGS. 1 through 16C illustrate various exemplary embodiments of a device 100 for obtaining a tissue sample. Referring to FIGS. 1 through 3, the device 100 has a base 101 made of two pieces, a first base component 102 and a second base component 103 that fit together to create a substantially cylindrical shape with a hollow interior with an open proximal end and an open distal end. FIGS. 1 through 3 also depict an exemplary embodiment of a driver 104 and two end effectors 105 and 106. While the end effectors 105, 106 described in the present application with reference to the figures are jaws, it should be understood that the end effectors can take any suitable form, such as, for example, cutters, forceps, manipulators or other suitable end effectors. The driver assembly can be attached to a sheath such as the spring sheath 107. The driver 104 is moveable in a proximal direction and a distal direction along a longitudinal axis that runs through the center of the base, and can be positioned by a drive wire 108 connected to a proximal end of the driver. The driver 104 can be made of a non-conductive material if electric current is not intended to run through it. The drive wire 108 can be made of any suitable material, such as, for example, any suitable metal or non-metal material.

Referring to FIG. 3, an exploded view of a driver assembly in accordance with an exemplary embodiment is illustrated. Driver 104 is depicted, as well as first base component 102 and second base component 103. Also depicted are jaw pieces 105, 106 with arms 109, 110 at the proximal ends shaped to engage with the driver and base components. A sheath 107, which can be a spring sheath or any other commercially available sheath, and a drive wire 108 are also illustrated. The driver can be made of stainless steel, or any other material that is commercially used in driver arms for endoscopic forceps tools. The base components can also be made of stainless steel, or other commercially available materials. The remaining components can be made of any materials that are commercially known to be used in the field of endoscopic graspers and tools, and drive wire associated with such tools.

Figure 4A:
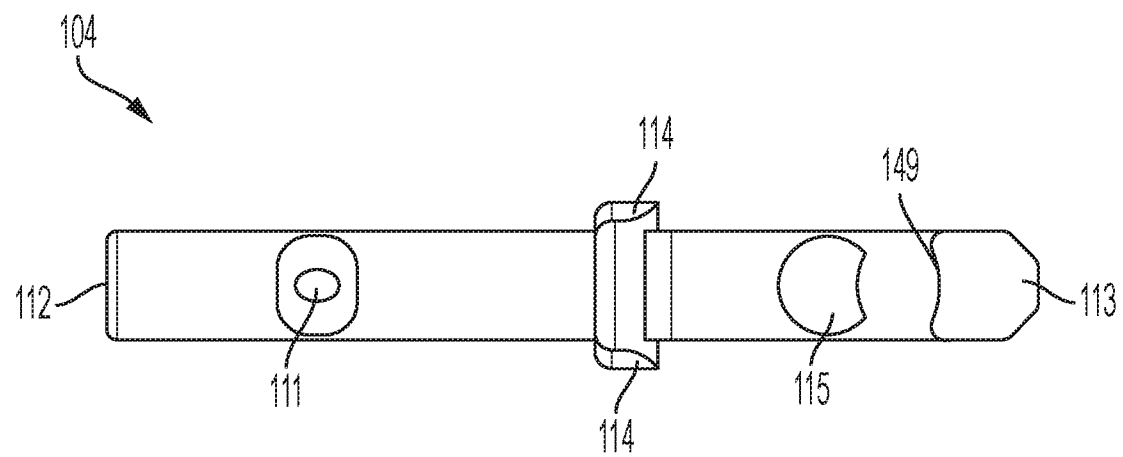
FIG. 4A depicts a side view of an exemplary embodiment of a driver having an exemplary embodiment of a stopper for the forceps of FIG. 1.
Figure 4B:
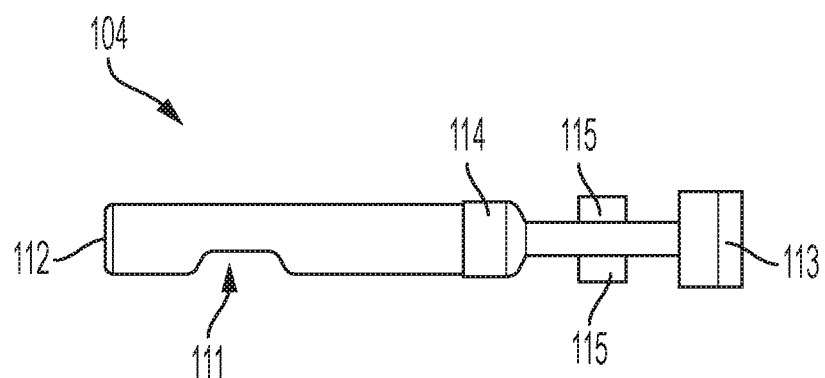
FIG. 4B depicts a top view of the driver of FIG. 4A.

FIG. 4A depicts a side view, and FIG. 4B depicts a top view, of a driver in accordance with an exemplary embodiment. The driver 104 is a substantially elongate member having a proximal end and a distal end. The proximal end of the driver can have an opening in the side 111, and an opening at the proximal end 112, to allow for a drive wire to be attached, and thus move the driver in both proximal and distal directions through a sheath and base.

The distal end of the driver includes an engagement feature 113 for engaging the jaws 105, 106. The engagement feature 113 can be one of a variety of shapes designed to abut and engage with the jaws. The distal portion of the driver as illustrated in FIG. 4A can have a narrower cross-sectional area than the proximal portion of the driver. Referring to FIGS. 4A and 4B, in certain embodiments, the driver 104 also includes two engagement features 115 that are disposed on a more proximal position of the driver as compared to the distal engagement feature 113. The engagement features 115 are also for engaging with the jaws 105 and 106. The driver 104 also has two stoppers 114 extending therefrom that are positioned to engage with the base 101 to prevent the driver 104 from moving too far distally when the jaws 105, 106 are to be opened, and from moving too far proximally when the jaws 105, 106 are to be closed.

Figure 5A:
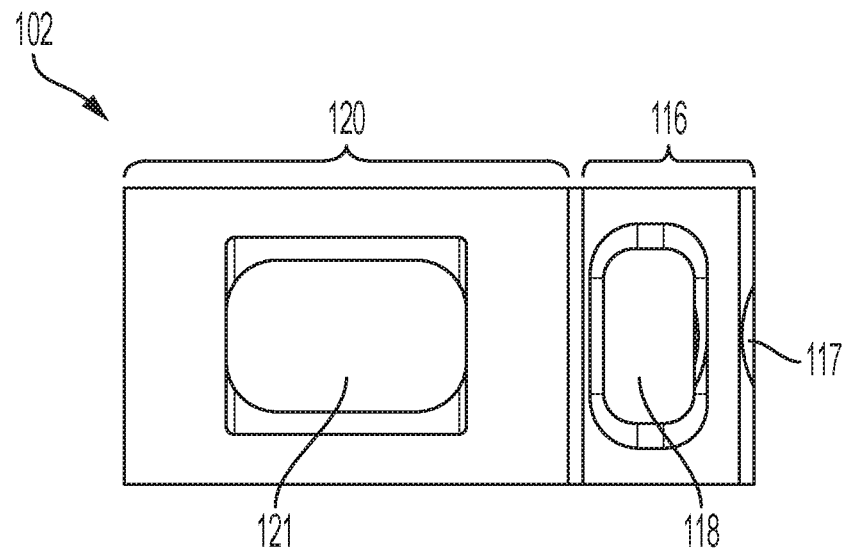
FIG. 5A depicts an outside view of an exemplary embodiment of a base component for the forceps of FIG. 1.
Figure 5B:
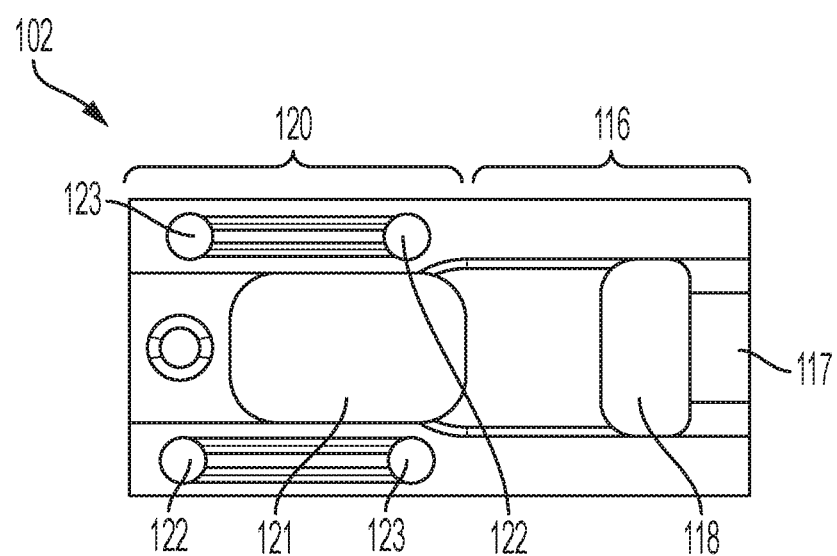
FIG. 5B depicts an inside view of an exemplary embodiment of a base component for the forceps in FIG. 1.

FIGS. 5A and 5B illustrate an exemplary embodiment of the components 102, 103 that make up the base 101 of the driver assembly for forceps according to an exemplary embodiment. FIG. 5A illustrates the outer surface of a base component 102. FIG. 5B illustrates an inside view of a base component 102. The curvature of the surface is evident in the perspective illustrations in FIGS. 10A and 10B. The distal portion 116 of the base components 102, 103 has an opening 118 for the proximal end of a jaw 105, 106 to fit into and pivot about. The proximal portion 120 of the base components 102, 103 have a proximal opening 121 for receiving the stoppers 114 of the driver 104. That is, proximal opening 121 is sized for a stopper 114 to fit at least partially through, in a direction perpendicular to a longitudinal axis of the assembly. FIG. 5B further illustrates pins 122 and indentations 123 of one base component 102 that interlock with aligned pins and indentations on the second base component 103. The distal portion 116 of the base 101 also has a distal ring 117 which can be used to provide pivot points for end effectors as they open and close. Base component 103 can be identical to base component 102 in accordance with an exemplary embodiment.

Figure 5C:
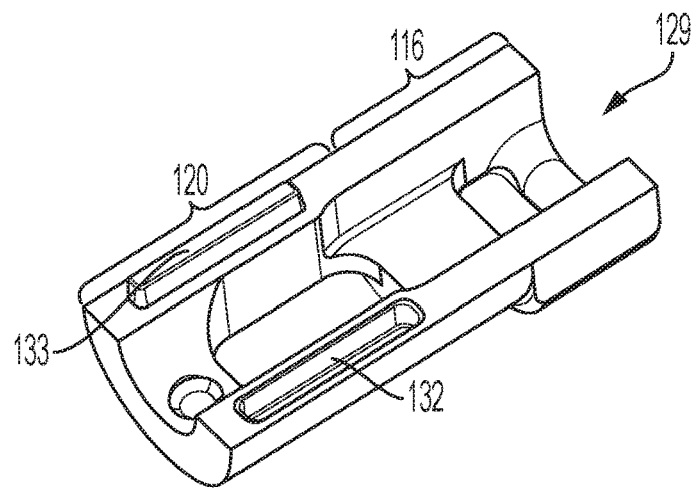
FIG. 5C depicts a perspective view of another exemplary embodiment of a base component for the forceps of FIG. 1.
Figure 5D:
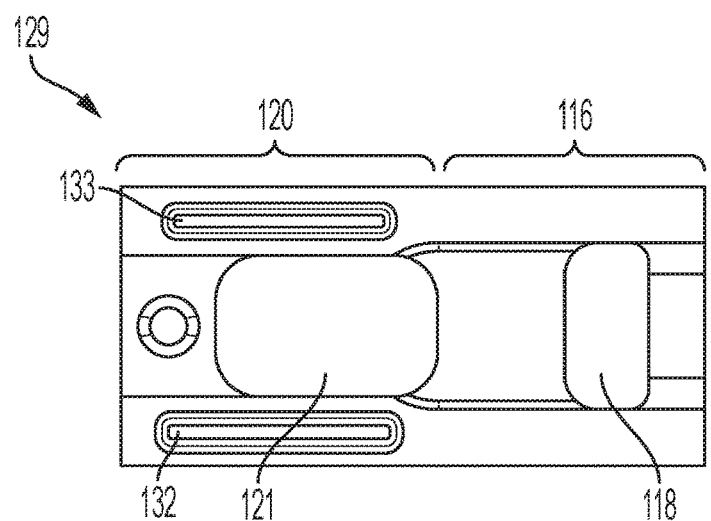
FIG. 5D depicts an inside view of the base component of FIG. 5C.
Figure 5E:
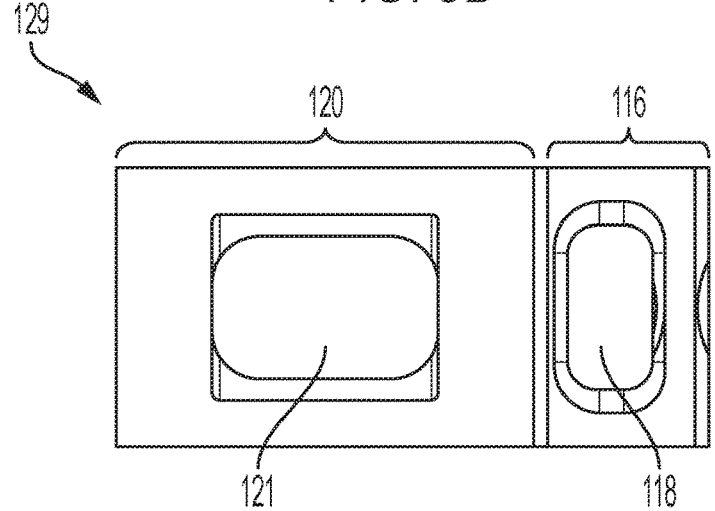
FIG. 5E depicts an outside view of the base component of FIG. 5C.

FIGS. 5C-5E illustrate another exemplary embodiment of a base component 129. As with the embodiment illustrated in FIGS. 5A and 5B, two identical base components 129 can interlock together to comprise the base, and can be used instead of base components 102, 103. Base component 129 has substantially the same shape and openings as base component 102. Two base components 129 can fit together by interlocking pieces. Each base component 129 can have an indentation (not shown) on one side of the distal portion 116 which forms a snug fit with protrusion (not shown) on the other side of the distal end 116 of the base component. In the illustrated embodiment, indentation 132, on the proximal portion 120 of the base component, forms a connecting fit with protrusion 133, located on the proximal portion 120 of the other base component. The end effector internal arms 109, 110 interlock with distal openings 118, and the stopper 114 interlocks with proximal openings 121 of the base component as described herein with respect to base component pieces 102 and 103.

Figure 11:
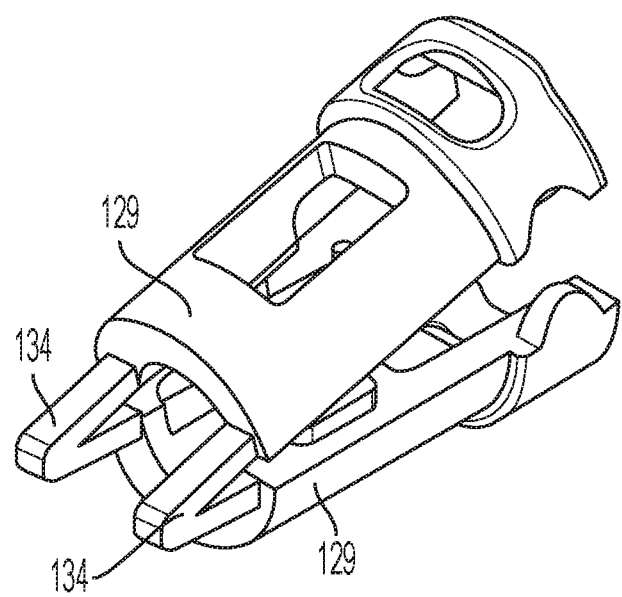
FIG. 11 depicts a perspective view of an exemplary embodiment of a connector for connecting to the base components of FIG. 11.
Figure 12:
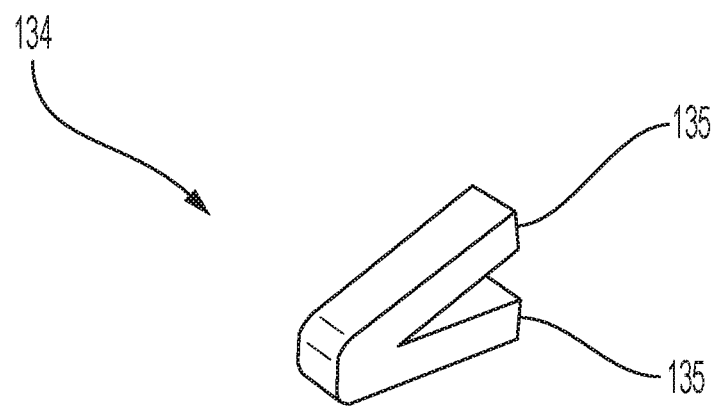
FIG. 12 depicts an exemplary embodiment of a connector element for the base components of FIG. 11.

Referring to FIG. 11, an embodiment of a connector 134 for base components 129 is illustrated. The connector 134 can be made of fluorinated ethylene propylene or other polymers that do not conduct electric current, or can be made of the same material as the base components. The base components can take the form of base components 129 illustrated in FIGS. 5C-5E, or can take the form of base components 102, 103 illustrated in FIGS. 5A-5B. FIG. 12 illustrates a single connector element 134 independent from the base components 12. The connector is formed and flexible, and can have a substantially "v" shape, with the bend of the "v" defining a proximal end and two legs extending toward a distal end. The connector is open at the distal end and closed at the proximal end. The distal end of the connector is where the connector is connected to the base component, with one leg 135 connected to a proximal end of each base component 129. The connectors assist in assembly of the device, in particular the assembly of the base components onto the driver 104 and end effectors 105, 106. The connector 134 can be made by pouring a polymer into a mold, or it can be made by any other known method.

Figure 13A:
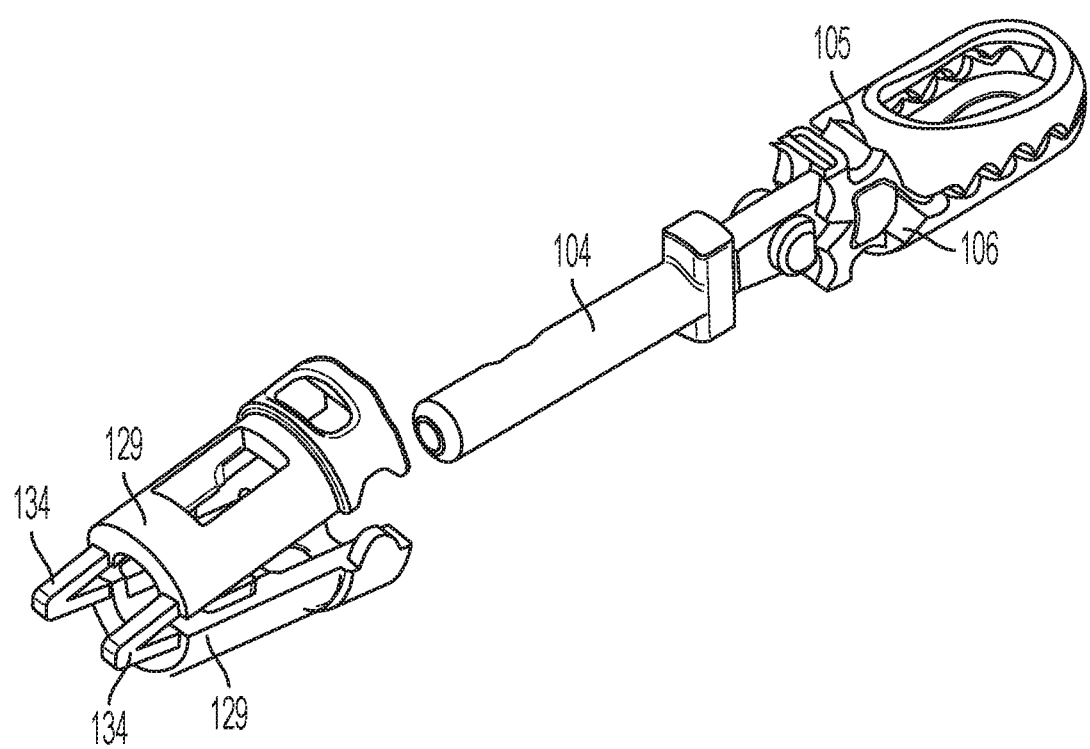
FIGS. 13A-13C depict stages of assembly of the forceps of FIG. 1 with the connected base components of FIG. 11 and the connector element of FIG. 12.
Figure 13B:
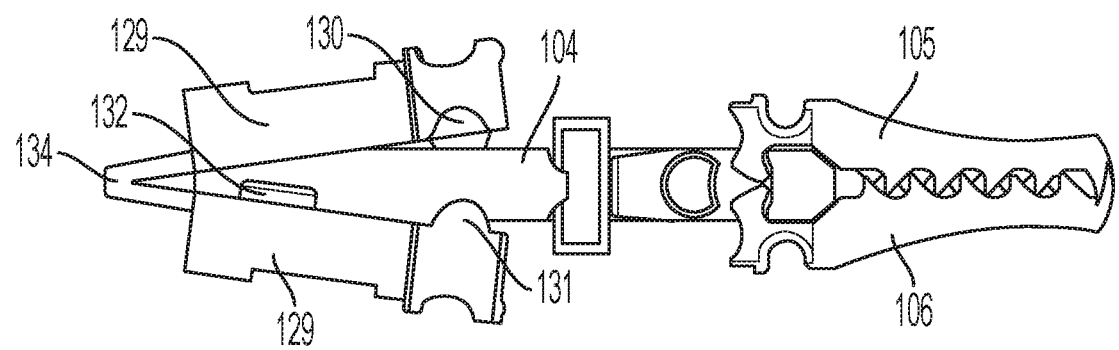
Figure 13C:
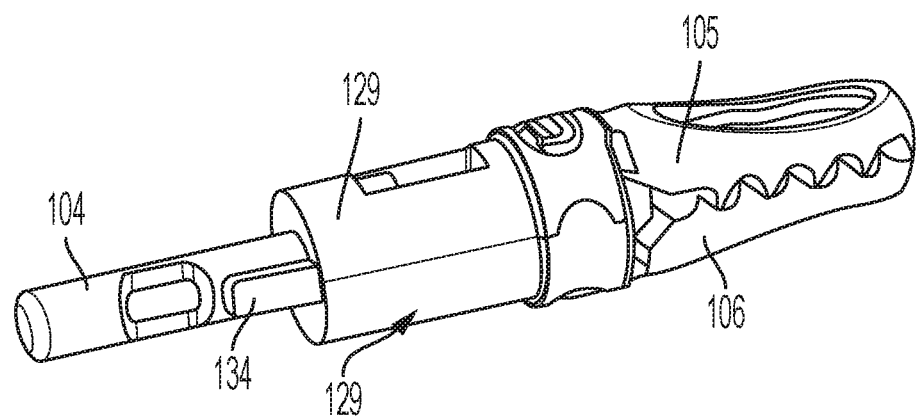

As illustrated in FIG. 13A, the jaws 105, 106 have been assembled over the distal end of the driver 104. The base components 129 have been connected to each other with connectors 134, and while in an open configuration, the base components 129 are ready to be placed over the drive arm 104. FIG. 13B illustrates the base components when moved into a position such that they are surrounding the drive arm 104 and still in an open configuration. The protrusions and indentations on the base components 129 can be those described with reference to FIGS. 5C through 5E. Referring to FIG. 13B, the protrusions of one base component have not yet come into contact with the indentations of the other base component. In some embodiments, the base components can be welded together. The connectors 134 assist the protrusions and indentations in attaining proper alignment when the base components 129 are moved into a closed position over the drive arm 104 and jaws 105, 106 as illustrated in FIG. 13C. When the base components 129 are moved into a closed position, the arms 109, 110 of the end effectors 105, 106 and the engagement features 113, 115 of the driver 105 are proximate to the distal openings 118 of the base components 129, and the stoppers 114, 115 of the driver 104 are in the proximal openings 121 of the base components 129. Once assembled, the connectors 134 can be removed from the base components 129. Removal of the connectors 134 from the base components 129 is not required.

Figure 14:
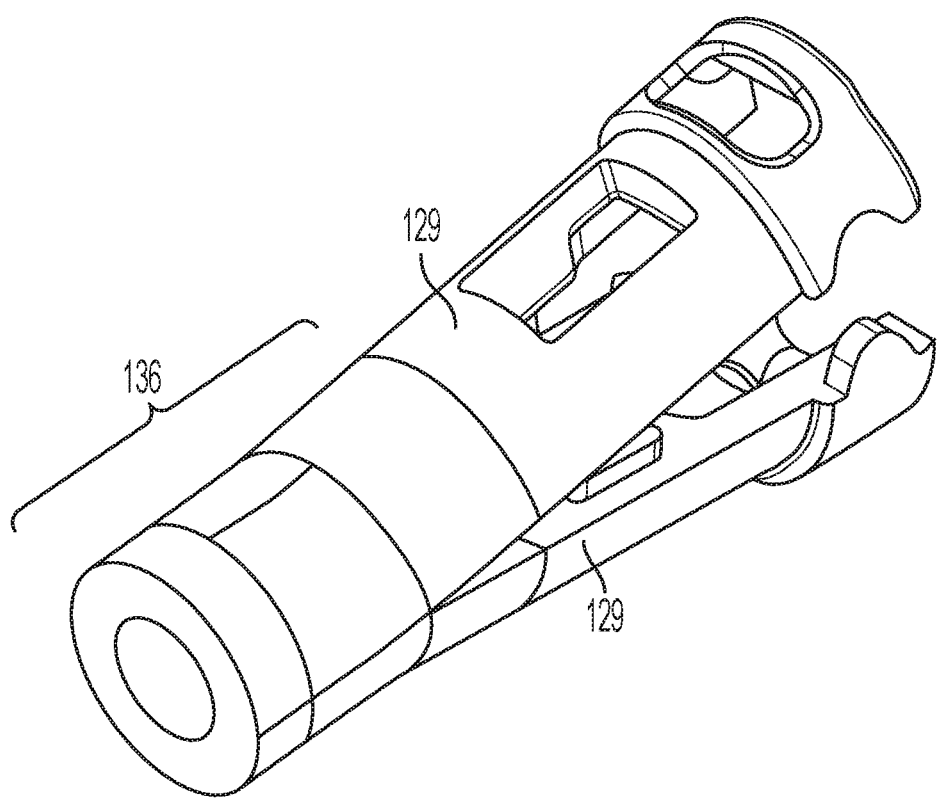
FIG. 14 depicts a perspective view of another exemplary embodiment of connected base components.
Figure 15:
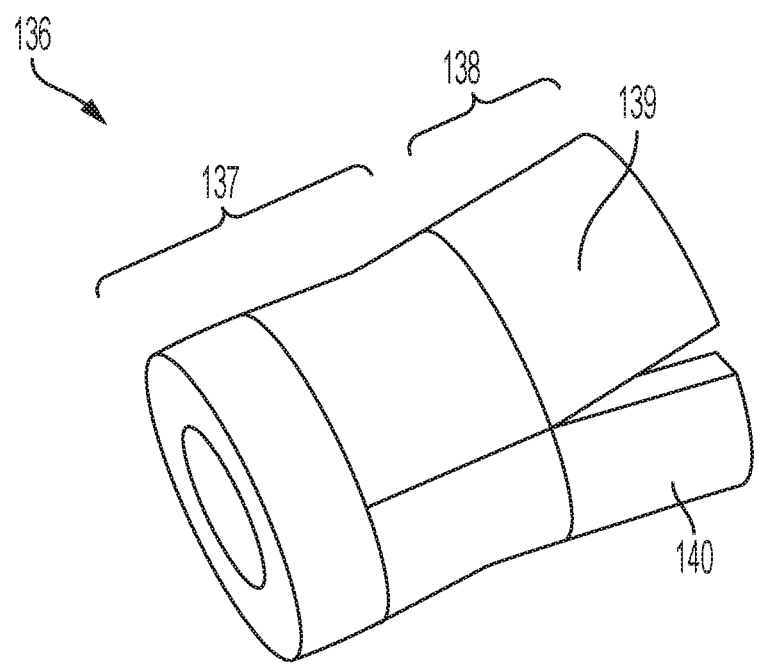
FIG. 15 depicts an exemplary embodiment of a connector element for the base components of FIG. 14.

FIG. 14 illustrates an exemplary embodiment of a split-fork bendable joint 136 that can be used to assist in clamping together base components 129. As illustrated in FIG. 15, bendable joint 136 has a proximal end 137 and a distal end 138. The proximal end 137 can have a cylindrical shape with a lumen running therethrough, of a size sufficient to fit over a proximal end of a drive arm. The distal end 138 can be the split-fork end of the split-fork bendable joint, and can have a cylindrical shape when in a closed position but can separate along the split so that two separate pieces 139 and 140 are angled away from each other along a longitudinal axis, but remain joined to the proximal portion 137. Referring again to FIG. 14, the distal end pieces 139, 140 of the split-fork bendable joint 136 can be attached to the proximal ends of the base components 129. The split fork ends 139, 140 can be secured to the base components 129 in any reasonable manner. In an exemplary embodiment, they can be molded to, or glued to, or welded to the base component. The proximal portion 137 can be a barrel. The barrel can have varying lengths. The split-fork bendable joint can be made of fluorinated ethylene propylene or any material that does not conduct electric current and has flexibility to it.

Figure 16A:
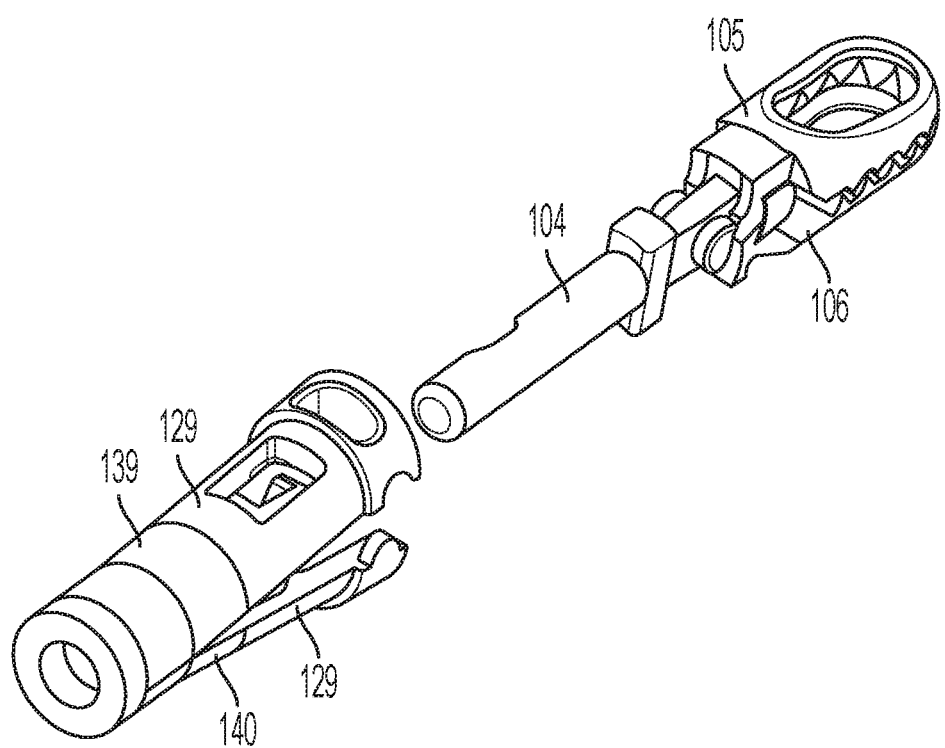
FIGS. 16A-16C depict stages of assembly of the forceps of FIG. 1 with connected base components of FIG. 14 and the connector element of FIG. 15.
Figure 16B:
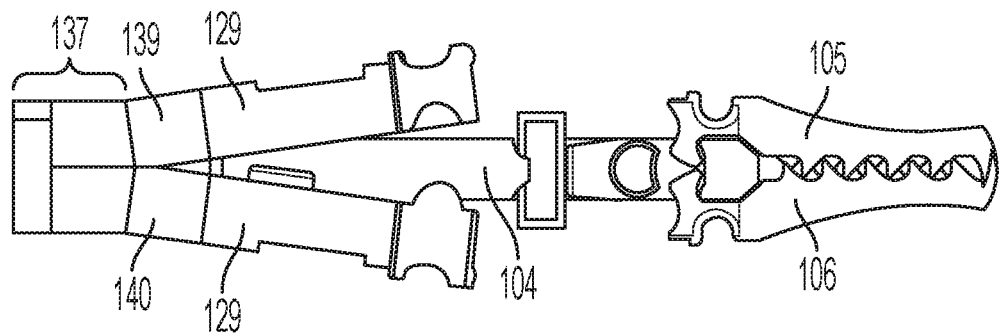
Figure 16C:
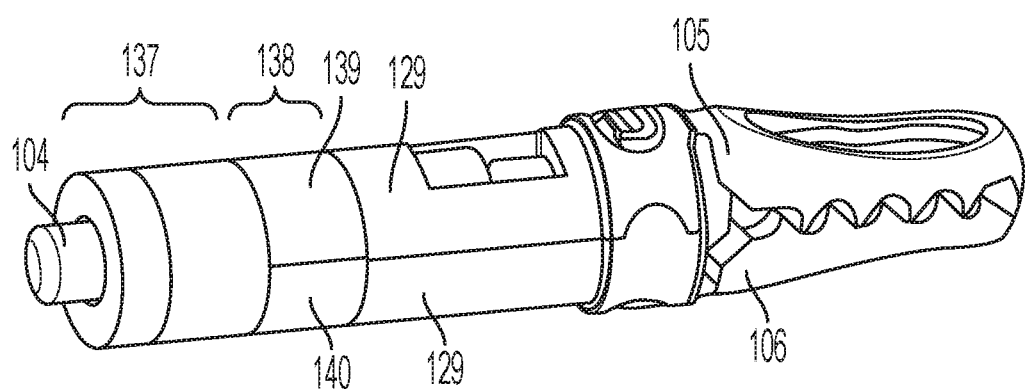

As illustrated in FIG. 16A, the end effectors 105, 106 have been assembled over the distal end of the driver 104. The distal end pieces 139, 140 of the split-fork bendable joint 136 have been secured to the proximal ends of the base components 129, but remain in an open configuration. FIG. 16B illustrates the base components when moved into a position such that they are surrounding the drive arm 104 and still in an open configuration. Protrusions and indentations on the base components 129 can be those of FIGS. 5C-5E in an exemplary embodiment. Referring to FIG. 16B, the protrusions of one base component have not yet come into contact with the indentations of the other base component. In certain embodiments, the base components can be welded together. The split-fork bendable joint 136 assists the protrusions and indentations attain proper alignment when the base components 129 are moved into a closed position over the drive arm 104 and jaws 105, 106 as illustrated in FIG. 16C. When the base components 129 are moved into a closed position, the arms 109, 110 of the end effectors 105, 106 and the engagement features 113, 115 of the driver 104 are proximate the distal openings 118 of the base components 129, and the stoppers 114, 115 of the driver 104 are in the proximal openings 121 of the base components 129.

The use of the connectors and a split-fork bendable joint described herein is not limited to forceps, and may be used for a more efficient assembly process of endoscopic tools and biopsy graspers.

A slip ring (not shown) can be used in an exemplary embodiment to hold together base components 129 during the assembling and/or welding process. The slip ring can be used independently of, or in conjunction with, a connector or a split-fork bendable joint.

Figure 8A:
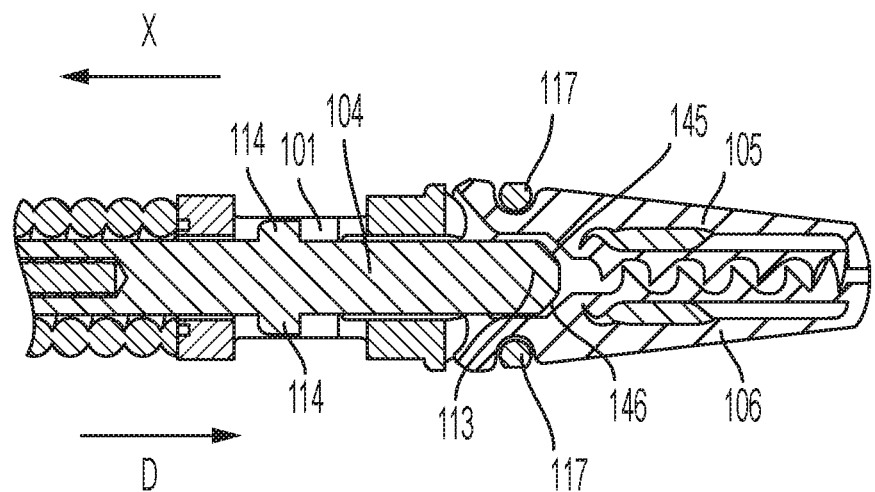
FIGS. 8A and 8B depict cross-sectional side views of the forceps of FIG. 1 with base and driver of FIG. 7A in the first and second positions, respectively.
Figure 8B:
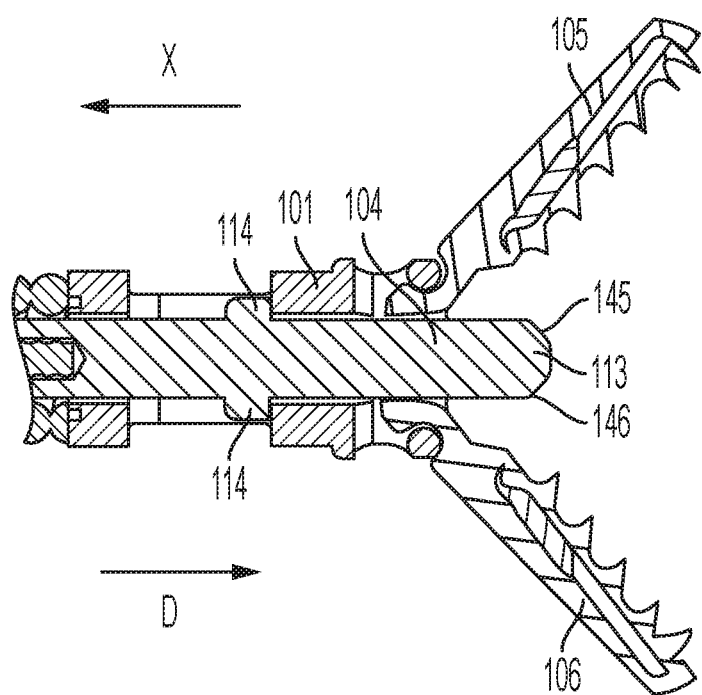

Referring to FIGS. 8A through 8B and FIGS. 17 through 21, the end effectors 105, 106 are moved from a closed position (as shown in FIG. 8A) to an open position (as shown in FIG. 8B) by moving the driver 104 in the direction D, and the end effectors are moved from the open position to the closed position by moving the driver 104 in the direction X. When the end effectors 105, 106 are in the closed position, the engagement feature 113 at the distal end of the driver 104 is positioned to engage an angled surface 217 of the end effectors 105, 106, and the one or more engagement features 115 (FIGS. 4A and 4B) are positioned to engage the arms 109, 110 (FIGS. 17-21) of the end effectors 105, 106. In the illustrated embodiment, the engagement feature 113 has angled surfaces 145, 146 for engaging the angled surface 217 of the end effectors 105, 106. Movement of the driver 104 in the direction D causes the distal engagement feature 113 to engage the angled surface 217 of the end effectors 105, 106 and causes the one or more engagement features 115 to engage the arms 109, 110 of the end effectors 105, 106. Movement of the driver 104 in the direction X causes the engagement feature 113 to engage the arms 109, 110 to facilitate movement of the end effectors 105, 106 to the closed position.

Figure 17:
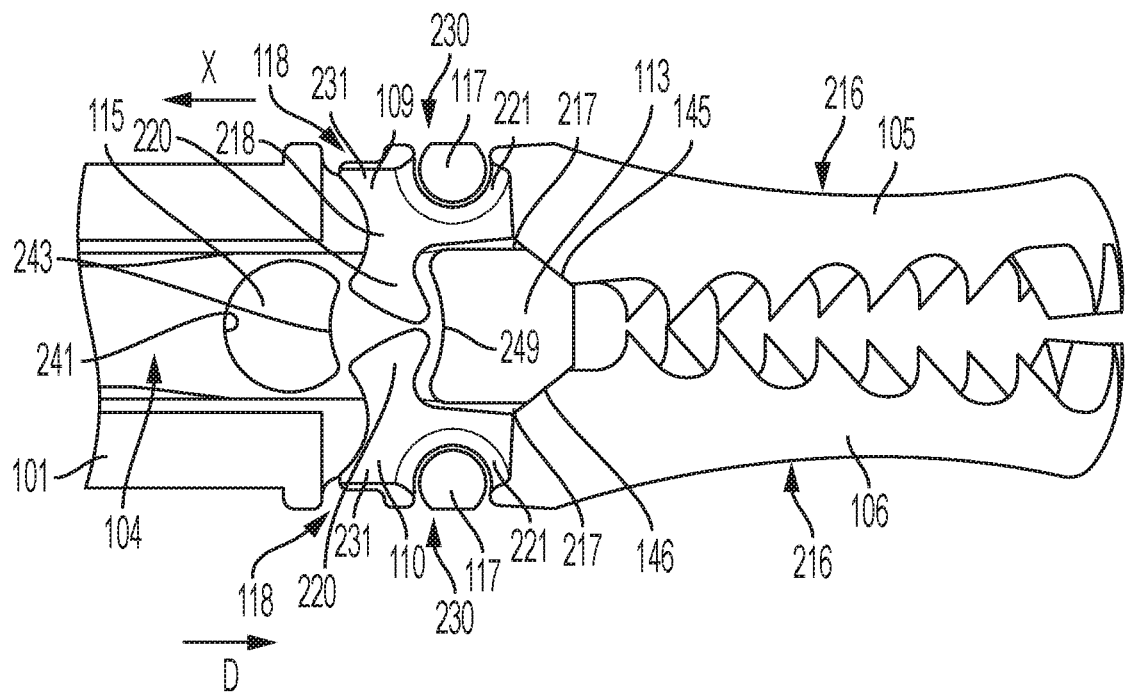
FIGS. 17-21 depict the engagement between the driver of FIG. 4A and the jaw components of FIGS. 6A and 6B for the forceps of FIG. 1.

Referring to FIG. 17, in the illustrated embodiment, the end effectors 105, 106 are a pair of jaws that include a first jaw 105 and a second jaw 106. Each jaw 105, 106 has a proximal portion 230 and a distal portion 216, in which the proximal portion 230 is connected to the base 101, and in which the distal portion 116 extends in a distal direction away from the base 101. The proximal portion 230 of both the first jaw 105 and the second jaw 106 includes at least one arm 109, 110 for connecting to the base 101. The arms 109, 110 can include an inwardly extending piece 220, an outward extending protrusion 231, a proximately located curved portion 218, and an outward curved portion 221. When the jaws 105, 106 are connected to the base 101, an outer ring 117 of the base 101 is disposed in the outward curved portion 221 of the arms 109, 110 such that the jaws 105, 106 can pivot about the outer ring 117 of the base. The inwardly extending piece 220 extends into the hollow interior of the base 101 such that the engagement features 113, 115 of the driver 105 can engage the arms 109, 110. In certain embodiments, the outward extending protrusion 231 extends into an opening 118 at the distal portion of the base 101 such that the outward extending protrusion 231 does not extend outward beyond the outer wall of the base 101 when the jaws 105, 106 pivot between the open and closed positions.

Still referring to FIG. 17, the driver 104 includes a first engagement feature 113 and a second engagement feature 115. In certain embodiments, the first engagement feature 113 has distal portion having angled surfaces 145, 146 and a proximal portion having a concave proximal surface 249, and the engagement feature 115 a round proximal surface 241 and a concave distal surface 243. The concave distal surface 243 of the engagement feature 115 is configured to engage the arms 109, 110 to cause the arms 109, 110 of the end effectors 105, 106 such that the arms 109, 110 to pivot about the base 101 without becoming locked or jammed. For example, concave distal surface 243 of the engagement feature 115 is configured to engage the proximately curved proximal portion 218 of the arms 109, 110 to cause the arms 109, 110 to pivot about the base 101, which prevents the arms 109, 110 from locking or jamming. Similarly, the concave proximal portion 249 of the engagement feature 113 is configured to engage the arms 109, 110 when the end effectors 105, 106 are being moved to a closed position such that the arms 109, 110 pivot about the base 101 without becoming locked or jammed. In certain embodiments, the round proximal surface 241 of the engagement feature 115 are configured to engage the proximately located curved portion 218 of the arms 109, 110 to prevent arms 109, 110 from pivoting once the end effectors 105, 106 are in a fully open position.

Figure 18:
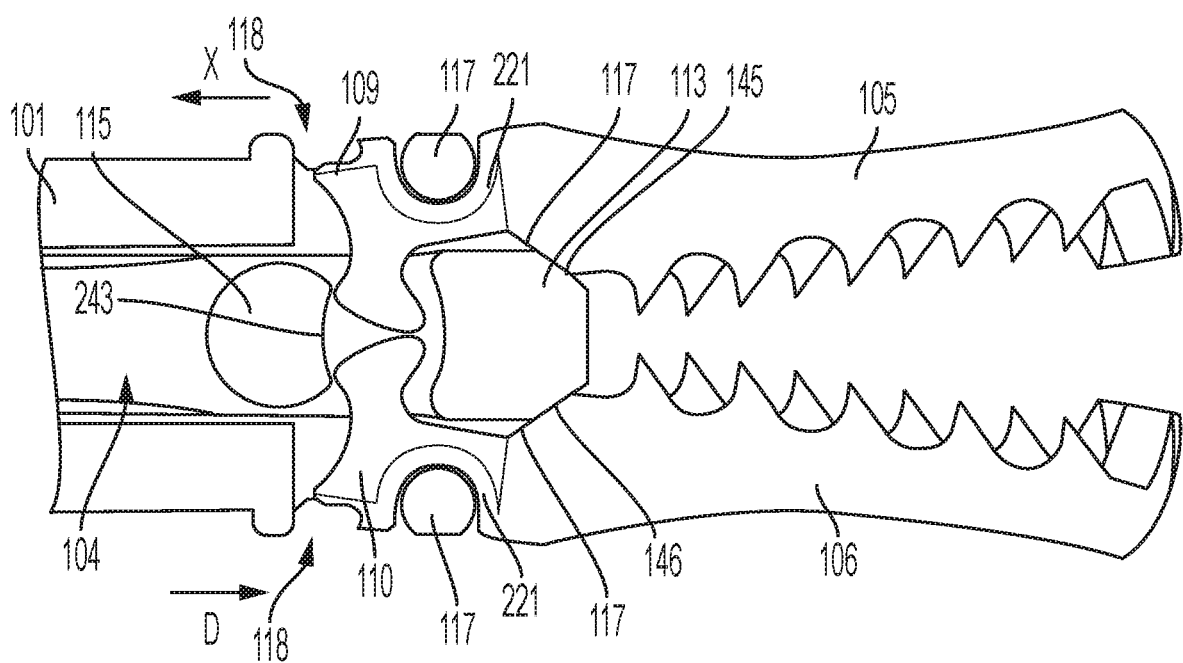
Figure 19:
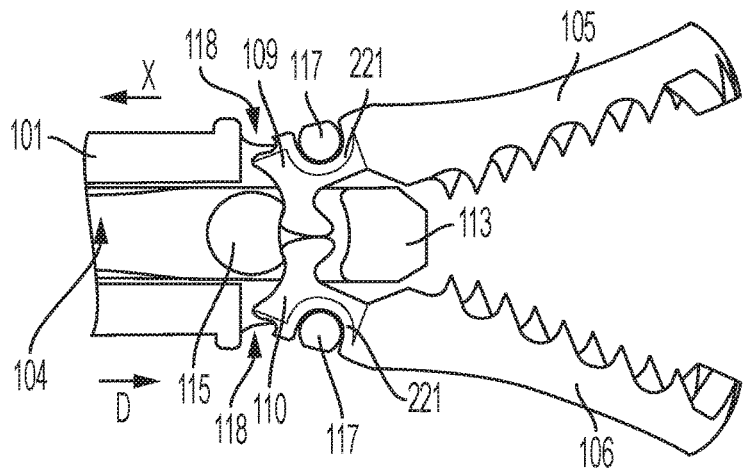

FIGS. 17 through 21 illustrate an exemplary embodiment of the engagement between the driver 104 and the end effectors 105, 106 to move the end effectors 105, 106 between the open and closed positions. Referring to FIG. 17, in an initial position, the first engagement feature 113 on the driver 104 is positioned to engage the angled surface 217 of each jaw 105, 106, and the second engagement feature 115 of the driver 104 is positioned to engage the arms 109, 110. Referring to FIG. 18, the driver 104 is moved in the direction D, which causes the engagement feature 113 to engage the angled surface 217 of the jaws 105, 106 and the move the jaws 105, 106 to a first partially-opened position. Referring to FIG. 19, the continued movement of the driver 104 in the direction D causes the engagement feature 115 to engage the arms 109, 110 to cause the arms 109, 110 to pivot about the ring 117 of the base 101 such that jaws 105, 106 move to a second partially-opened position. In the second partially-opened position, the engagement feature 113 is no longer engaging the jaws 105, 106 and is extended into the area between the distal portion 216 of each jaw member 105, 106.

Figure 20:
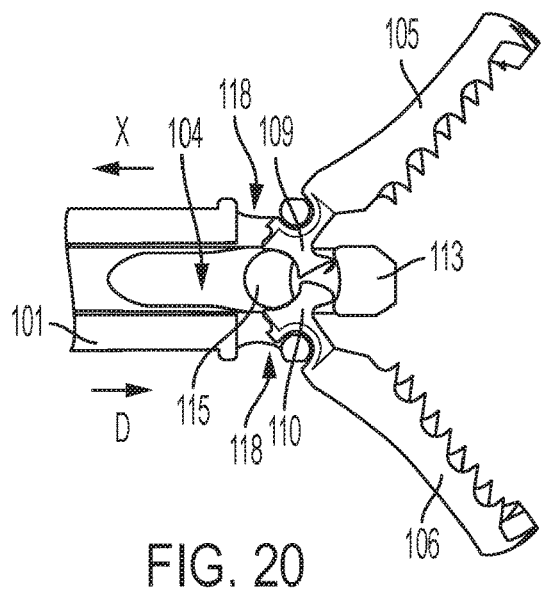

Referring to FIG. 20, the driver 104 is moved in the direction D until the jaws 105, 106 are in the fully-opened position. In certain embodiments, when the jaws 105, 106 are in the fully opened position, the engagement feature 115 locks the jaws 106, 107 into position such that the jaws are not capable of opening any further. When the jaws 106, 107 are closed (as shown in FIG. 8A), the interior angle between the jaws is about zero (0) degrees, and when the jaws are fully opened (as shown in FIG. 20), the interior angle between the jaws is at a maximum, which can range from about eighty-five (85) degrees to about one hundred ten (110) degrees.

Figure 21:
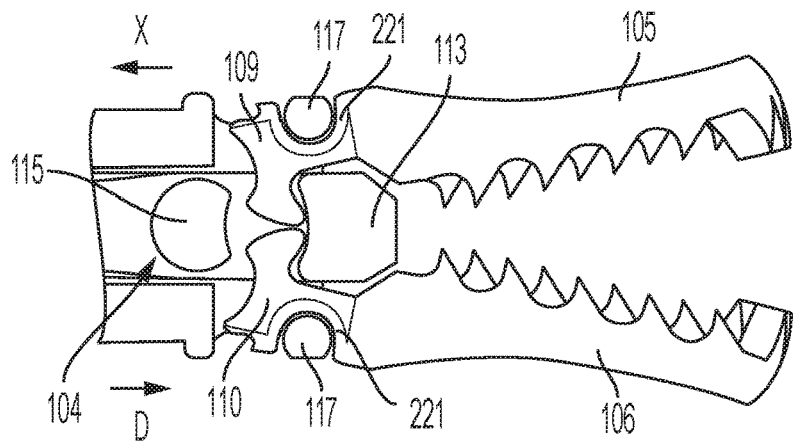

FIG. 21 illustrates the jaws 105, 106 beginning to move from an open position to the closed position. In the illustrated embodiment, driver 104 is pulled in a proximal direction X, which causes the engagement feature 113 of the driver 104 to engage the inwardly facing arms 109, 110 such that the arms 109, 110 are pushed in a proximal direction, thereby causing the curved portion 221 of the jaws to pivot around the ring 117 of the base 101. Thus the jaws pivot and close, and the angle between them decreases.

Figure 7A:
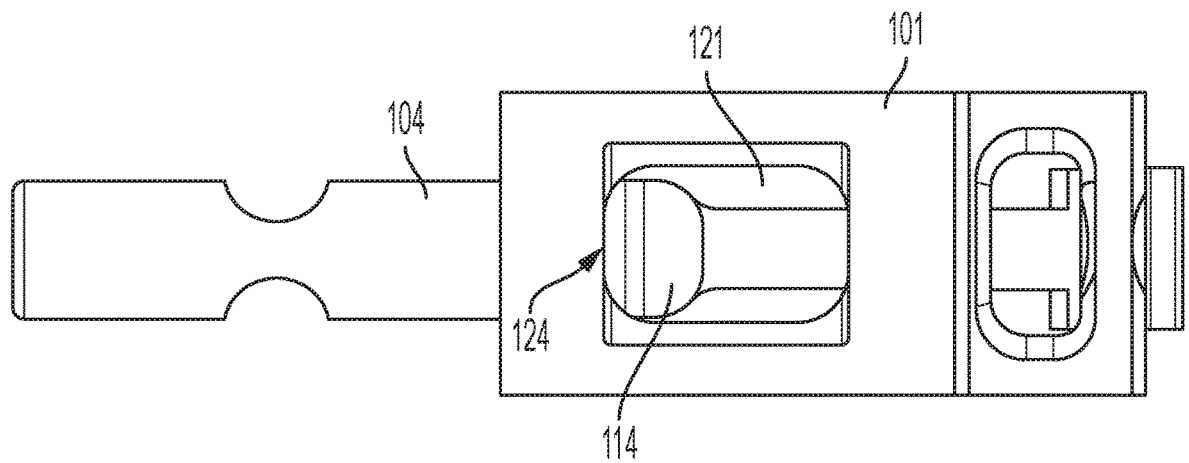
FIG. 7A depicts an exemplary embodiment of a base and an exemplary embodiment of a driver for the forceps of FIG. 1, in which the driver is in a first position relative to the base.
Figure 7B:
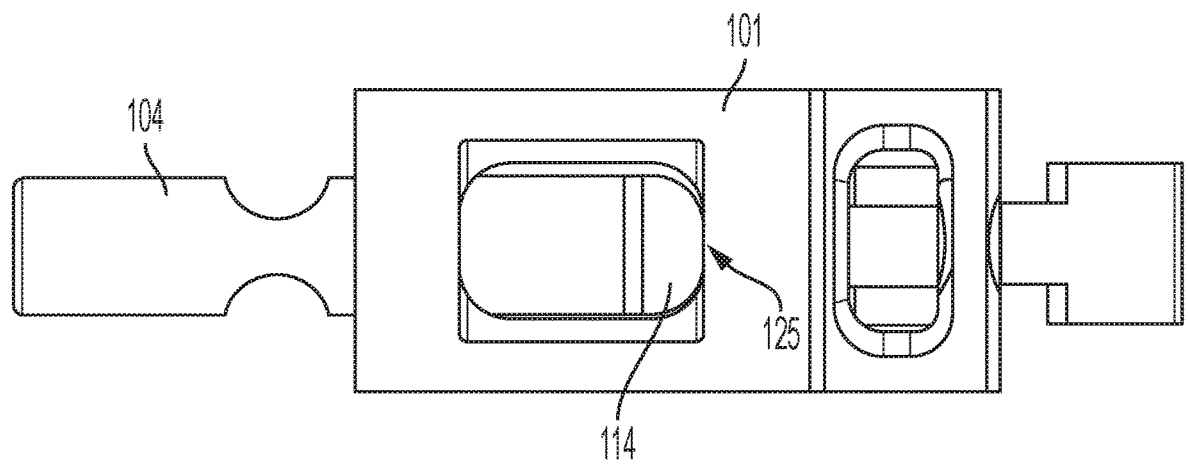
FIG. 7B depicts the base and driver of FIG. 7A, in which the driver is in a second position relative to the base.

Referring to FIGS. 7A and 7B, the stoppers 114, 115 are sized and shaped to fit within the openings 121 of the base 101. The stoppers 114 are configured to prevent the end effectors 105, 106 from disengaging the base 101 and/or the driver 104, and the stoppers 114 are configured to prevent over travel of the end effectors 105, 106 when the end effectors are moving to an open position. Referring to FIGS. 7A and 8A, when the stopper 114 is in a first position relative to the base 101 the stopper prevents the end effectors 106, 107 from disengaging. In the first potion, the stopper 114 engages a proximal side 124 of the proximal opening 121 of the base 101. Referring to FIGS. 7B and 8B, when the stopper 114 is in a second position relative to the base 101, the stopper prevents the end effectors from extending open past a fully open position. In the second position, the stopper 114 engages a distal side 125 of the proximal opening 121. That is, the engagement between the stopper 114 and the distal side 125 of the proximal opening 121 sets the maximum angle at which the end effectors can be opened, and prevents the application of too much force to open and unintentionally lock the end effectors in an open position due to disengagement of the end effectors from the base 101 and/or the driver 104.

Further, the single driver 104 and at least one stopper 114 allows the assembly to be used endoscopically, as there is no increase in the cross-sectional area, or diameter, of the components. There are no drive arms extending radially outward from the device, even when used in combination with an actuator assembly and drive wire to control the driver. There can be two stoppers 114.

Figure 6A:
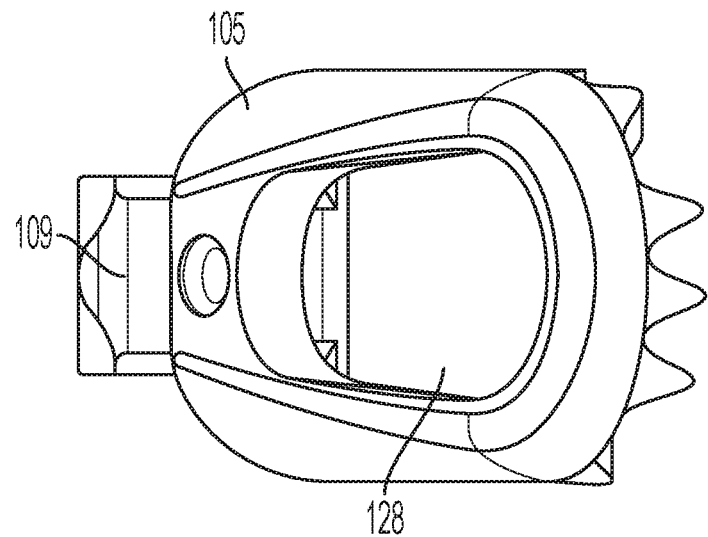
FIGS. 6A and 6B depict views of exemplary embodiments of jaw components for the forceps of FIG. 1.
Figure 6B:
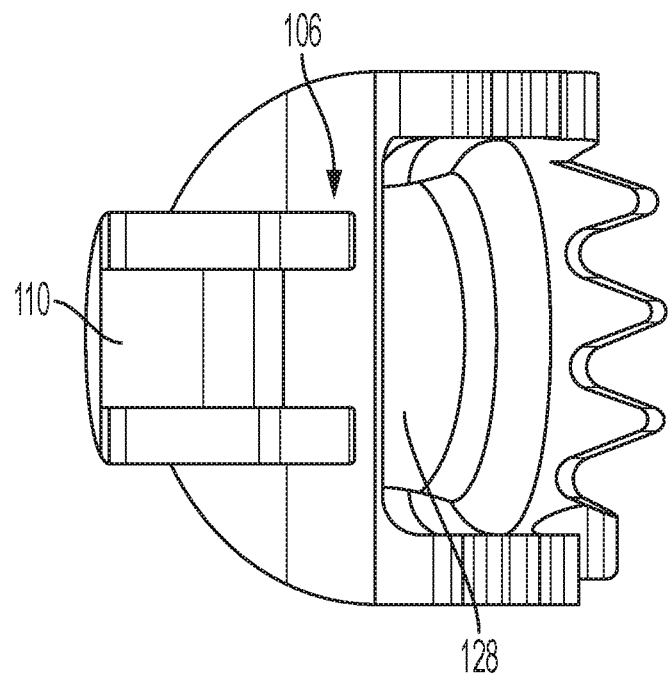

Referring to FIGS. 6A and 6B, jaw component 105, 106 in accordance with an exemplary embodiment are illustrated. The jaw components illustrated here are not meant to be limiting. Any end effector elements can be used instead of the jaws depicted in FIGS. 6A and 6B, such as any cups, grasper elements, sampling elements, biopsy elements, cutting elements, heat application elements, or drug delivery elements. FIG. 6A illustrates an outside view of a jaw element. FIG. 6B illustrates an inside view of a jaw element. Jaw components 105, 106 each have a proximal end, each with an inwardly extending arm 109 (or 110 on jaw component 106). The inwardly extending arms in an exemplary embodiment are of a size and shape to engage with openings 118 in the distal portion of the base 101, and such that the end effector portions of the jaws extend distally from an opening 126 at the distal end of the base. In certain embodiments, the arms 109, 110 do not extend beyond the outer wall of the base 101 when the end effectors are moved between the open and closed positions. These embodiments are advantageous because less protrusions are extending outward from a longitudinal axis of the base 101 (as compared to conventional forceps that include protrusions that extend outward when beyond the outer wall of the base) that could contact surrounding tissue during use of the device 100. End effectors can but are not required to have an opening 128.

In an exemplary embodiment, two jaw components are each moveable and can open and close, based on the position of the drive arm. In another exemplary embodiment, one jaw can be moveable and another jaw can be stationary. In this exemplary embodiment, the stationary jaw component can be fixedly attached to the base component. The drive arm and base component pieces can be adjusted to accommodate the fixed jaw component. The moveable jaw component can operate to open and close as described herein.

Figure 9A:
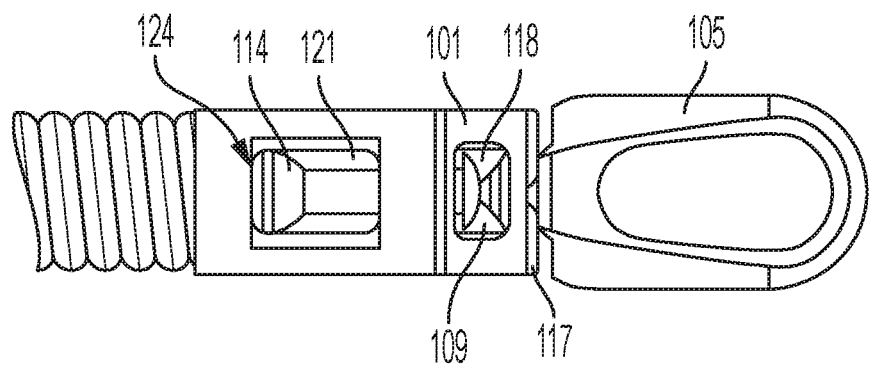
FIGS. 9A and 9B depict top views of the forceps of FIG. 1 with the base and drive of FIG. 7A in the first and second positions, respectively.
Figure 9B:
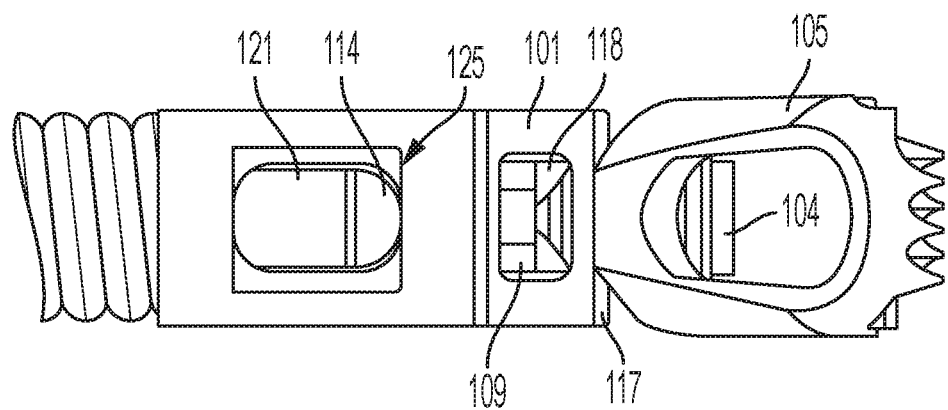

FIGS. 9A and 9B are top views of the device 100 in a closed position and open position, respectively. FIGS. 9A and 9B provide an additional illustration of how the components all fit together and engage with each other in both open and closed positions. In the closed position of FIG. 9A, the stopper 114 is against the proximal wall of the proximal opening 121 of the base 101. The distal opening 118 of the base 101 has a portion of the jaw arm 109 extending at least partially through it, such that the end effector can pivot about a distal ring portion 117 of the base 101. In FIG. 9B, the stopper and driver have both been pushed forward in a distal direction, and the end effectors 105, 106 are open. The stopper 114 is in contact with the distal portion of distal opening 125. The end effectors have pivoted around on the distal ring 117 of the base, and a lesser portion of the jaw arm 109 is extending through the opening 118 at the distal portion of the base. In FIG. 9B, the distal end of the driver 104 has extended out beyond the base 101 in a distal direction.

Figure 10A:
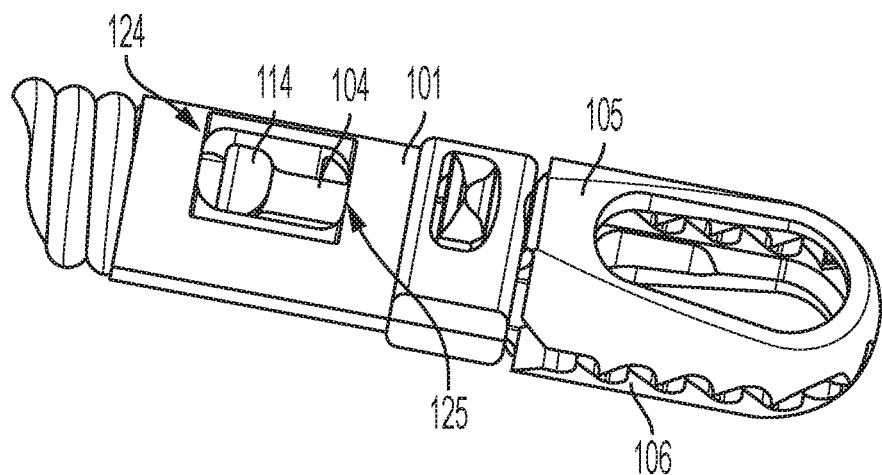
FIGS. 10A and 10B depict perspective views of the forceps of FIG. 1 with exemplary embodiments of end effectors in the closed and open positions, respectively.
Figure 10B:
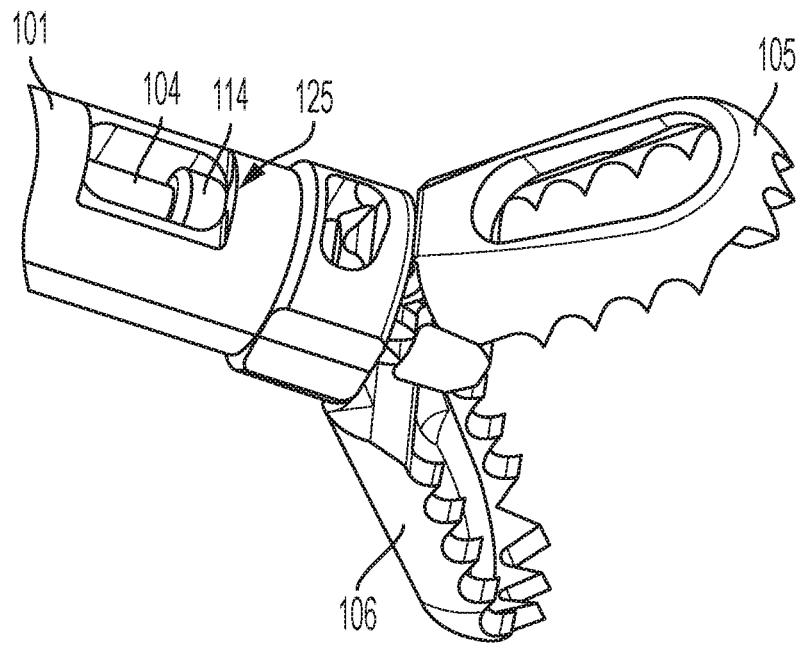

FIGS. 10A and 10B illustrate perspective views of the assembly in accordance with an exemplary embodiment. FIG. 10A is a top view of the assembly when the driver 104 is in a proximal position relative to the base 101, and the end effectors 105, 106 are closed. FIG. 10B is an illustration of when the driver is in a distal position relative to the base, and the end effectors are in the maximal open position they can be in, due to the restraint of the stopper against the distal wall of the opening 121 in the base.

In another exemplary embodiment, there can be three or four jaws. The base component and drive arm can be of size and shape to accommodate multiple jaws. In the embodiments of three or four jaws, there can be one fixed jaw, or all jaws open and close in accordance with the movement of the drive arm. The embodiments described herein are exemplary, and any end effector can be used for any of the fixed or moveable jaws, in any combination.

Accordingly, the various embodiments are not to be limited in scope by the specific embodiments described herein. Further, although some of the embodiments have been described herein in the context of a particular implementation in a particular environment for a particular purpose, those of ordinary skill in the art should recognize that its usefulness is not limited thereto and that the various embodiments can be beneficially implemented in any number of environments for any number of purposes. Accordingly, the claims set forth below should be construed in view of the full breadth and spirit of the embodiments as disclosed herein. While the foregoing description includes many details and specificities, it is to be understood that these have been included for purposes of explanation only, and are not to be interpreted as limitations of the various embodiments. Many modifications to the embodiments described above can be made without departing from the spirit and scope of this description.

The invention claimed is:

1. An endoscopic device, comprising:
a base having a first base component and a second base component, wherein both the first base component and the second base component have a proximal portion and a distal portion, wherein a proximal portion of both the first base component and the second base component includes an opening, wherein the first base component has one or more first base connectors and the second base component has one or more second base connectors, wherein the first base connectors are configured to operatively connect to the second base connectors such that the first and second base components form a cylindrical shaft with a hollow interior when the first base connectors are connected to the second base connectors;
a driver comprising a driver shaft, a proximal end, a distal end, and at least one stopper feature extending radially from the driver shaft, wherein the at least one stopper feature is movable within at least one of the openings of the first and second base components when the first base connectors of the first base component are connected to the second base connectors of the second base component; one or more end effectors connected to the distal portion of the base, wherein the one or more end effectors are operable to move between an open position and a closed positon by actuation of the driver; and
a connector configured to connect to a proximal end of each of the first base component and the second base component to hold the first and second base components together when the first base connectors are not connected to the second base connectors.

2. The endoscopic device according to claim 1, wherein the connector comprises a distal portion and a proximal portion, wherein the distal portion is split longitudinally into a first leg and a second leg, and the first and second legs are flexibly connected to the proximal portion; further wherein the first leg has a distal end connected to the proximal portion of the first base component portion and the second leg each has a distal end connected to the proximal portion of the second base component.

3. The endoscopic device according to claim 1, wherein the first and second legs are moveable between a closed position and an open position, wherein movement of the first and second legs to the closed position causes the first base connectors of the first base component and the second base connectors of the second base component to be connected such that the first and second base components form a cylindrical shaft with a hollow interior.

* * * * *